United States Patent [19]
Volk

[11] Patent Number: 5,523,810
[45] Date of Patent: Jun. 4, 1996

[54] INDIRECT OPHTHALMOSCOPY CONTACT LENS DEVICE WITH COMPOUND CONTACT LENS ELEMENT

[76] Inventor: Donald A. Volk, 9378 Jackson St., Mentor, Ohio 44060

[21] Appl. No.: 465,641

[22] Filed: Jun. 5, 1995

[51] Int. Cl.$^6$ ...................................................... A61B 3/00
[52] U.S. Cl. ........................................... 351/219; 351/205
[58] Field of Search ..................................... 351/219, 205, 351/212; 606/4, 5, 6

[56] References Cited

U.S. PATENT DOCUMENTS

| | | | |
|---|---|---|---|
| 3,158,677 | 11/1964 | Lacomme et al. | 88/57 |
| 4,410,245 | 10/1983 | Koester | 351/219 |
| 4,502,764 | 3/1985 | Riquin | 351/160 |
| 4,728,183 | 3/1988 | Heacock et al. | 351/219 |
| 4,768,866 | 9/1988 | Wickholm et al. | 350/410 |
| 5,007,729 | 4/1991 | Erickson et al. | 351/219 |
| 5,189,450 | 2/1993 | Crossman et al. | 351/219 |
| 5,200,773 | 4/1993 | Volk | 351/219 |
| 5,309,187 | 5/1994 | Crossman et al. | 351/219 |

FOREIGN PATENT DOCUMENTS

| | | | |
|---|---|---|---|
| 686760 | 3/1994 | Japan | 351/219 |
| 2008787 | 3/1994 | U.S.S.R. | 351/219 |

*Primary Examiner*—William L. Sikes
*Assistant Examiner*—James A. Dudek
*Attorney, Agent, or Firm*—Spencer & Frank

[57] ABSTRACT

An indirect ophthalmoscopy contact lens device includes a contact lens having a first posterior lens surface with a concave shape substantially corresponding to the shape of an average cornea and an image forming lens for collecting and focussing light exiting the patient's eye and entering the contact lens when in place on the patient's eye for forming an aerial image of the fundus of the patient's eye. The contact lens comprises a compound contact lens element including a posterior lens portion cemented to an anterior lens portion. The posterior lens portion includes the first posterior lens surface and a first anterior lens surface, and is made of a material having a first index of refraction and a first Abbe value. The anterior lens portion has a second posterior lens surface with a shape substantially matching a shape of the first anterior lens surface and a second anterior lens surface having a convex shape. The anterior lens portion is made of a material having a second index of refraction and a second Abbe value. At least one of the second index of refraction and the second Abbe value is different from the first index of refraction and the first Abbe value, respectively. The optical cement preferably has an index of refraction corresponding to the first or second index of refraction.

37 Claims, 4 Drawing Sheets

INDIRECT OPHTHALMOSCOPY CONTACT LENS DEVICE WITH COMPOUND CONTACT LENS ELEMENT

BACKGROUND OF THE INVENTION

The invention relates to an indirect ophthalmoscopy contact lens device for observing and treating the fundus of a patient's eye in conjunction with a slit lamp biomicroscope as well as for use in vitreoretinal surgery in conjunction with an operating microscope. Such a device includes a contact lens element and an image forming lens system mounted in a housing, with the image forming lens system being anterior of the contact lens element. The contact lens element has a concave posterior surface with a profile substantially corresponding to the shape of the average cornea for placement on the patient's eye. Light emanating from the patient's retina passes through the contact lens element and is refracted by the image forming lens system to form an aerial image of the patient's fundus anterior of the image forming lens.

An ophthalmoscopic contact lens device of this type is disclosed, for example, in my prior U.S. Pat. No. 5,200,773. The indirect ophthalmoscopy contact lens system described in this patent includes a meniscus contact lens element and a high refractive index biconvex imaging lens combined to provide a very wide field, high resolution image of the fundus, well suited for both fundus observation and pan retinal photocoagulation laser treatment.

U.S. Pat. No. 5,007,729 to Erickson et al, describes a three element ophthalmoscopic contact lens including an entry lens, a contact lens, and a center lens in spaced apart relationship. The center lens is a biconvex lens made of high refractive index optical material. The lens disclosed in this patent provides a wide field of view but suffers from additional surface reflections from its multiplicity of lens surfaces.

While indirect ophthalmoscopy contact lenses made according to the above mentioned patents function satisfactorily, I have continued my efforts to develop even wider-field ophthalmoscopic contact lenses with improved resolution and image clarity, and as well, enhanced depth of field and optical performance, with minimal surface reflections degrading the image and extensive correction of field curvature, astigmatism and distortion.

SUMMARY OF THE INVENTION

It is therefore an object of the present invention to provide an improved indirect ophthalmoscopy contact lens device which not only has a wide field of view but also has improved image quality and minimal surface reflections.

The above and other objects are accomplished according to the invention by the provision of an indirect ophthalmoscopy contact lens device including a contact lens having a first posterior lens surface with a concave shape substantially corresponding to the shape of an average cornea and an image forming lens for collecting and focussing light exiting the patient's eye through the contact lens when in place on the patient's eye for forming an aerial image of the fundus of the patient's eye, wherein the contact lens comprises a compound contact lens element including a posterior lens portion including the first posterior lens surface and a first anterior lens surface, the posterior lens portion being made of a material having a first index of refraction and a first Abbe value; an anterior lens portion having a second posterior lens surface with a shape substantially matching a shape of the first anterior lens surface and a second anterior lens surface having a convex shape, the anterior lens portion being made of a material having a second index of refraction and a second Abbe value, at least one of the second index of refraction and the second Abbe value being different from the first index of refraction and the first Abbe value, respectively; and an optical cement having a third index of refraction corresponding to one of the first and second indexes of refraction for fixing in intimate contact the second posterior lens surface to the first anterior lens surface.

According to one embodiment of the invention, the anterior lens portion is biconvex and itself comprises the image forming lens. According to a further embodiment of the invention there is additionally provided a housing, wherein the compound contact lens element is mounted in the housing and the image forming lens comprises a separate lens system mounted in the housing spaced apart in an anterior direction from the compound contact lens element.

The indirect ophthalmoscopy contact lens device according to one aspect of the invention utilizes a compound contact lens element in combination with an imaging lens system to provide a wide field of view of a patient's retina. The compound contact lens element according to this aspect of the invention comprises a high index of refraction anterior lens portion made of either glass or plastic, and which is preferably made of glass and a relatively low index of refraction posterior lens portion made of either glass or plastic, and which is preferably made of plastic. The glass anterior lens portion preferably has an index of refraction in a range from about 1.52 to about 2.1, and most preferably in a range from about 1.7 to about 1.9. The plastic posterior lens portion preferably has an index of refraction in a range from about 1.3 to 1.52 and most preferably is made from polymethylmethacrylate having an index of refraction of about 1.491. According to a further aspect of the invention, the difference between the index of refraction of the anterior lens portion and posterior lens portion of the contact lens element is equal to or greater than 0.27.

According to yet another aspect of the invention, in order to capture the most peripheral rays exiting the eye, the high index anterior glass portion is brought as close as possible to the corneal surface. Thus, the center thickness of the posterior lens portion should be as thin as practically possible. In a preferred embodiment of the invention, the center thickness of the posterior lens portion will be in a range from about 0.125 to 2.0 millimeters and in a more preferred embodiment of the invention, the center thickness will be in a range from about 0.125 to about 0.75 millimeters.

The two components of the contact lens element, i.e., the posterior lens portion and the anterior lens portion, are glued together at their mating surfaces with the use of an optical glue preferably having an index of refraction substantially corresponding to the index of refraction of either the posterior lens portion or the anterior lens portion. The posterior surface of the posterior lens portion will have a concave shape with a profile corresponding to that of the average cornea. The anterior surface of the posterior lens portion may have either a plano, convex or concave shape to match the plano, concave or convex posterior surface, respectively, of the anterior lens portion. Due to the high index of refraction of the glass anterior lens portion relative to the plastic posterior lens portion, a substantial amount of light bending will occur at the interface of the two lens portions as light rays exiting the posterior lens portion and enter the anterior lens portion, bringing the extreme peripheral rays exiting the eye towards the image forming lens to contribute to the formation of the aerial image anterior of the image forming lens. The index of refraction of the glass anterior lens portion will preferably be as high as possible without being so high as to have the resulting color dispersion or chromatic aberration degrade the image or interfere with laser treatment properties of the lens device. Light reflection that would otherwise occur at the interface of the two index different portions may be eliminated through the use of a thin film anti-reflection coating, index matched to the optical cement and applied to the portion whose index of refraction differs from that of the optical glue. Additionally, the surfaces of the anterior image forming lens system may be coated to minimize reflection and enhance laser beam transmission.

According to another embodiment of the invention, the lens device may include a plus powered middle lens element, preferably meniscus-shaped, for the purpose of providing an even wider field of view by bending the most peripheral light rays exiting the eye toward the optical axis of the device so as to be collected and focussed in the aerial image by the image forming lens.

According to another aspect of the invention, the compound contact lens element comprises a highly dispersive minus powered posterior lens portion and a plus powered anterior lens portion with reduced dispersion in order to provide an indirect ophthalmoscopy contact lens system with reduced or minimized chromatic aberration, for superior visualization and laser treatment, especially in the central retinal area. The anterior portion has an Abbe value in a range from about 40 to 90 and the posterior portion has an Abbe value in a range from about 20 to 50.

According to yet another aspect of the invention, the posterior focus of the lens system is located behind the patient's eye pupil, and within the crystalline lens or vitreous humor, thus reducing the distance between the compound contact lens element and the imaging lens in order to reduce the total length of the lens system and housing, and additionally to bring the anterior focus less far from the patient's eye.

Other features, advantages and benefits of the invention will become apparent from the ensuing description when considered in connection with the accompanying drawings.

DETAILED DESCRIPTION OF THE PREFERRED EMBODIMENTS

Figure 1:
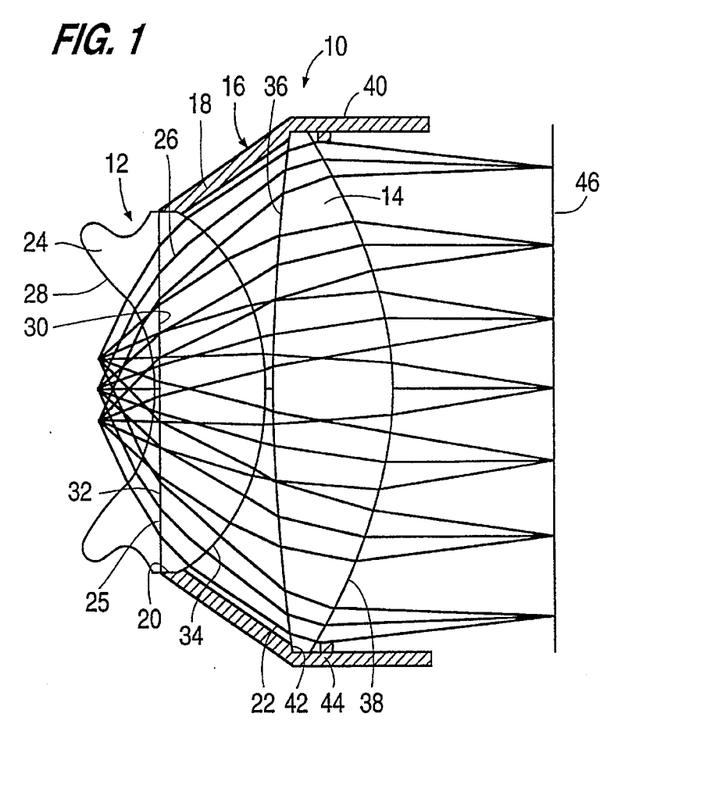
FIG. 1 is a side sectional view of an indirect ophthalmoscopy contact lens device incorporating a compound contact lens element and a separate image forming lens, together with a ray tracing, according to one embodiment of the invention.

Referring to FIG. 1, there is shown an indirect ophthalmoscopy contact lens device 10 which, according to one embodiment of the invention, includes a compound contact lens element 12 and an image forming lens 14 mounted in a housing 16. Housing 16 has a frustoconically shaped portion 18 presenting a first open end 20 having a smaller diameter than a second, opposite open end 22. Contact lens element 12 is mounted in the first, smaller diameter open end 20 and image forming lens 14 is mounted in the larger diameter open end 22. Image forming lens 14 is thus in an anterior position relative to contact lens element 12 when device 10 is in use on a patients eye.

Contact lens element 12 is a compound lens element including a posterior lens portion 24 glued to an anterior lens portion 26. Posterior lens portion 24 has a concave posterior surface 28 which has a curvature corresponding to the curvature of the average cornea and is thus adapted for placement on a patient's eye. Posterior lens portion 24 has an anterior surface 30 which, in the embodiment of FIG. 1, is shown as planar. Anterior lens portion 26 has a posterior surface 32 which is shaped to match the anterior surface 30 of posterior lens portion 24 and is thus, in the embodiment of FIG. 1, also planar. Anterior lens portion 26 has an anterior surface 34 which is convex in shape. Image forming lens 14 has a convex posterior surface 36 and a convex anterior surface 38.

Housing 16 has an extension 40 connected to the wide diameter end of frustoconically shaped portion 18 in a manner which defines a shoulder 42 against which image forming lens 14 rests. Image forming lens 14 is held in place by a screw down retaining ring 44 or other suitable means.

In accordance with one embodiment of the invention, the posterior lens portion 24 of contact lens element 12 is made of a material having a low index of refraction compared to a higher index of refraction material comprising the anterior lens portion 26. In general, it is the difference in index of refraction between posterior lens portion 24 and anterior lens portion 26 that determines the amount of light bending at the interface of these two lens portions. Therefore, the greater the difference, the greater the bending, and ultimately, the wider the field of view of the fundus that is presented in the image at plane 46. Preferably, the index of refraction of posterior lens portion 24 will be in a range from about 1.3 to 1.52 and the index of refraction of anterior lens portion 26 will be in a range from about 1.52 to about 2.1, and most preferable in a range from about 1.7 to about 1.9, and the difference between the indices of refraction of the two lens portions will preferably be equal to or greater than 0.27. As an example, posterior lens portion 24 can be made of polymethylmethacrylate (PMMA) having an index of refraction of 1.491 or of other, even lower index optical materials. Anterior lens portion 26 can be made of a high index of refraction glass such as LAH58 Lanthanum glass manufactured by O'Hara Corporation having an index refraction of 1.883. In general, the high index glass anterior lens portion 26 should be made of a material having as high an index of refraction as possible without being so high as to have high dispersion or chromatic aberration which would degrade the image or interfere with laser treatment properties of the lens. Another suitable glass having less color dispersion than LAH58 has the commercial designation LAL59 also manufactured by O'Hara and has an index of refraction of 1.734.

An optical glue 25 used for fixing anterior surface 30 of posterior lens portion 24 to posterior surface 32 of anterior lens portion 26 should have an index of refraction which closely matches the index of refraction of either the posterior lens portion 24 or anterior lens portion 26. A suitable optical glue that may be used for this purpose is manufactured by Summers Laboratories under the designation SK-9 and has an index of refraction of approximately 1.5, which closely matches the index of refraction of the PMMA material from which the posterior lens portion 24 can be made.

In order to capture the most peripheral rays exiting the eye, and thus to increase the field of view, it is important to bring the high index glass anterior lens portion 26 as close to the corneal surface as possible while still maintaining the integrity of the low index posterior lens portion 24. Moreover, as many high index glasses are subject to attack from acids and bases and may also be prone to chipping and breakage, the protective qualities of the plastic posterior lens portion serve to eliminate these problems while still allowing the high index glass to be essentially as close to the cornea as possible. Further, the optical advantages of the present invention, including resolution and image clarity at large pupil diameters would not be possible if the entire contact lens element were made from a high index glass due principally to the high negative curvature required at the corneal contacting surface. In accordance with the invention, the posterior lens portion of the contact lens element will preferably have a center thickness in a range from about 0.125 to about 2.0 mm, and more preferably in a range from about 0.125 to about 0.5. From a practical manufacturing standpoint, the center thickness of the posterior lens portion may be minimized by gluing an uncut posterior lens portion having the correct anterior surface profile to the anterior lens portion having the correct mating surface and subsequently generating and polishing the posterior lens surface of the posterior lens portion until the desired thickness and surface profile are achieved.

Figure 2:
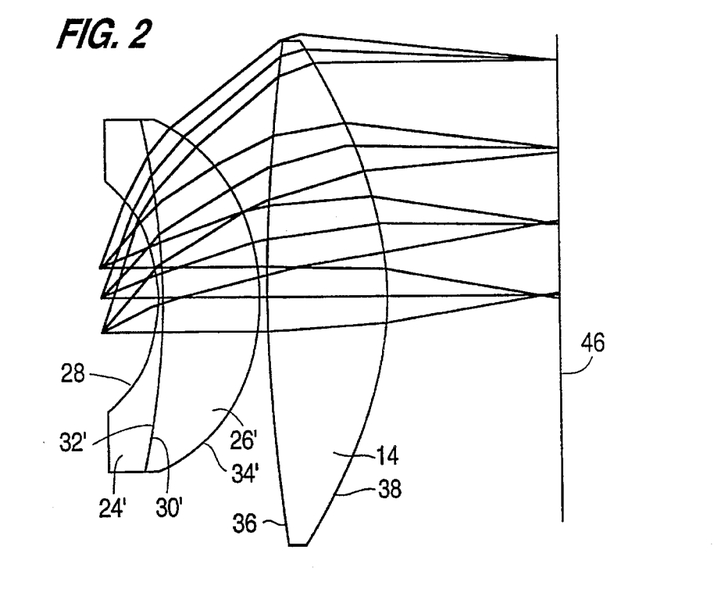
FIG. 2 is a diagram showing a lens layout and ray tracing according to a modified embodiment of the invention shown in FIG. 1.
Figure 3:
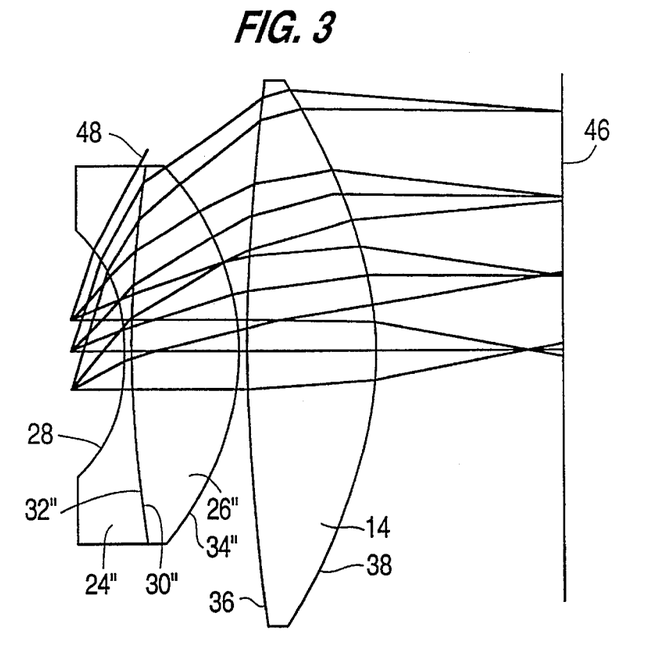
FIG. 3 is a diagram showing a lens layout and ray tracing according to another modified embodiment of the invention shown in FIG. 1.

Although the mating surfaces of posterior lens portion 24 and anterior lens portion 26 are shown as plano in FIG. 1, the mating surfaces may be curved as shown in FIGS. 2 and 3 discussed below. In general, there are optical advantages to having the mating surfaces less highly curved than the corneal surface.

Desirably, the convex anterior surface 34 of posterior lens portion 26 may be aspheric in order to optimally maintain high resolution and image clarity over a wide range of pupil diameters, including very large pupil diameters. Alternately, for simplicity in manufacturing, aspherical curve may be utilized. Furthermore, a cap (not shown) made of either glass or plastic material, having a posterior surface matching the anterior surface of the anterior portion may be cemented to the anterior lens portion. The anterior surface of the cap may be of spherical or aspherical configuration to provide further optical correction as desired.

Advantageously, one or both surfaces of the image forming lens may be aspheric, as similarly described in my prior U.S. Pat. No. 5,200,773. The formula $$z = \frac{cr^2}{1 + \sqrt{1-(1+k)c^2r^2}} + a_1 r + a_2 r^2 + a_3 r^3 \ldots$$

has been utilized in defining the aspheric surfaces of this invention, where z equals the surface sag along the lens axis, c equals the curvature (i.e., reciprocal of the radius), r is the radial coordinate in lens units, k equals the conic constant, and $a_n$ (where n=1,2,...) is the coefficient value of any of the selected conic deformation terms.. Although the use of coefficient values has been limited to only two examples, tailoring of any of the lens surfaces of this invention through the use of coefficient terms may be accomplished as desired.

In an exemplary construction of an indirect ophthalmoscopy contact lens device as shown in FIG. 1, posterior lens portion 24 is made of PMMA having an index of refraction of 1.49, with a center thickness of 0.25 mm and an eyelid flange diameter of 15.5 mm. Posterior surface 28 has a 7.7 mm apical radius with a conic constant of −0.18. Anterior surface 30 of posterior lens portion 24 is plano and thus has an infinite radius of curvature. Anterior lens portion 26 is made of LAH58 glass having an index of refraction of 1.883. Posterior surface 32 of anterior lens portion 26 has a matching plano surface and a convex anterior surface 34 having an apical radius of 10 mm with a conic constant of −0.25. Anterior lens portion 26 has a center thickness of 6 mm and a diameter of 16.6 mm. Image forming lens 14 is spaced from contact lens element 12 by 0.5 mm and is also made of LAH58 glass. The posterior surface 36 of image forming lens 14 has an apical radius of 100 mm with a conic constant of −8.0. Anterior surface 38 of image forming lens 14 has an apical radius of 15 mm with a conic constant of −2.0 and a sixth order coefficient term of 0.00000003. Image forming lens 14 has a diameter of 26 mm and a center thickness of 7 mm. When an ophthalmoscopy lens system with these parameters is placed on an emmetropic eye with the fundus serving as a light source, an aerial image will be produced approximately 9.0 mm anterior of the image forming lens. By virtue of its relatively high lateral magnification and 8.854 mm focal length, the lens of this embodiment will produce a high resolution wide field fundus image providing enhanced laser photocoagulation treatment of the far peripheral retina, especially in the treatment of proliferative diabetic retinothopy and retinal vein occlusion, while simultaneously minimizing laser energy concentration in the pupillary area or laser waist region.

Figure 4:
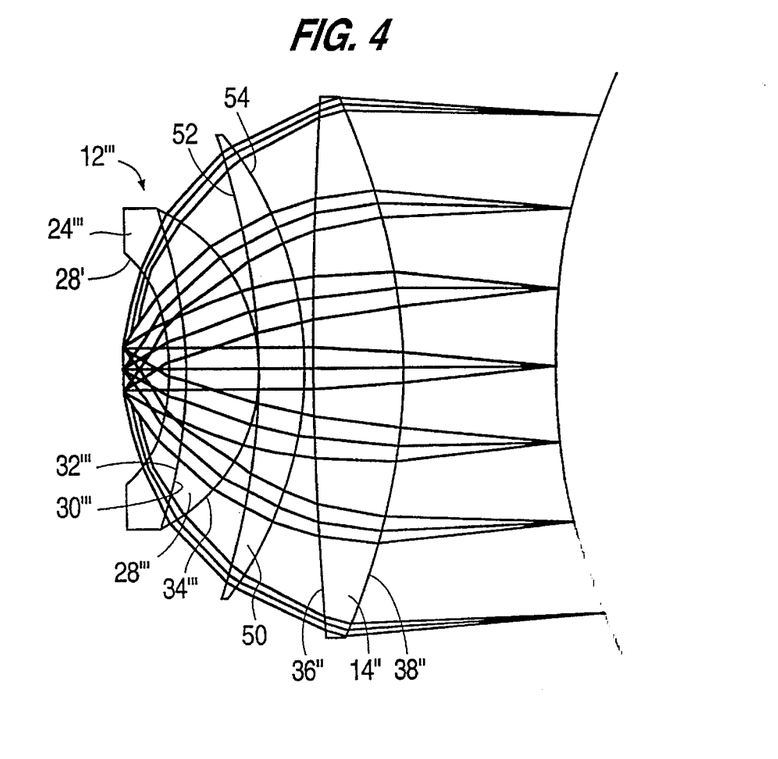
FIG. 4 is a diagram showing a lens layout including a middle meniscus lens, together with a ray tracing, according to a further embodiment of the invention.
Figure 5:
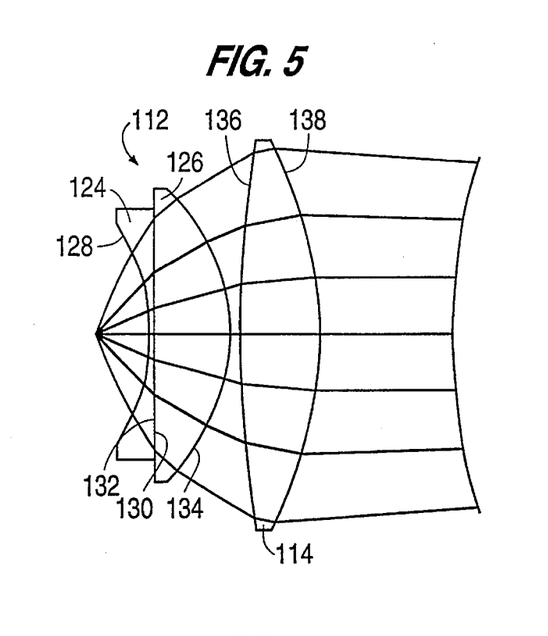
FIG. 5 is a diagram showing a lens layout and principal ray paths according to another embodiment of the invention.
Figure 6:
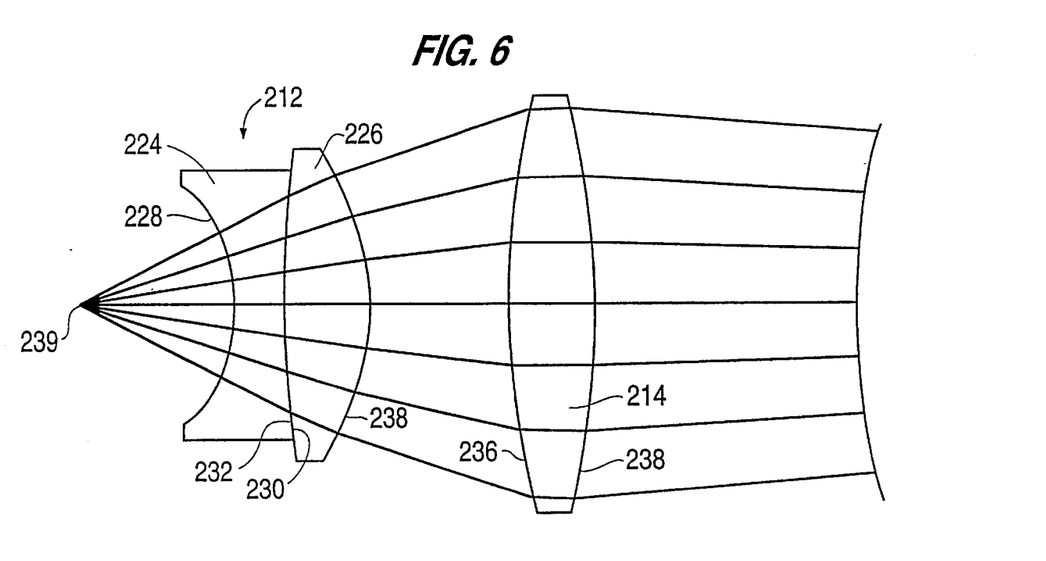
FIG. 6 is a diagram of another lens layout and principal ray paths according to a further embodiment of the invention.

FIGS. 1 through 7 illustrate the path of light rays through the optical lens system of this invention emanating from points on the retina (not shown) of an eye. In FIGS. 1–4 and 7, each ray bundle is represented by a principal ray and a peripheral ray on each side of the principal ray. In FIGS. 5 and 6 only the principal rays are shown.

Although shown as proceeding as parallel bundles from an entrance pupil location in air, the ray tracings through the lens system follow the same pathways as do light rays which originate at the retina and proceed through the vitreous humor, crystalline lens, aqueous humor and cornea of the eye to the various lens elements of the invention embodiments. The use of parallel bundles in air is a simplified representation of the more complex optical system of the emmetropic human eye, and is shown represented in all optical system layouts herein.

Referring again to FIG. 1, the change in the index of refraction between the lower index plastic posterior portion 24 and the higher index glass anterior portion 26 causes light rays exiting the eye to be bent inwardly toward the optical axis of device 10 at the interface of the two lens portions 24, 26 so that image forming lens 14 collects light rays emanating from the extreme peripheral portions of the retina and focuses these rays to provide a wide field image of the retina at image plane 46.

FIG. 2 is a diagram illustrating an alternative lens layout which could be used in place of the lens layout illustrated in FIG. 1, wherein like reference numerals in FIGS. 1 and 2 identify the same parts or surfaces. The only difference between the embodiment illustrated in FIG. 2 with respect to that illustrated in FIG. 1, is that in FIG. 2, posterior lens portion 24' has a convex anterior surface 30' and anterior lens portion 26' has a matching concave surface 32'. In an exemplary configuration of the embodiment of FIG. 2, the parameters are the same as in the exemplary embodiment described above in connection with FIG. 1 with the exception that the apical radii of curvature of surfaces 30' and 32' are each 35 mm, the center thickness of anterior lens portion 26' is 5.5 mm, and the anterior surface 34' of anterior lens portion 26' has an apical radius of 9.5 mm with a conic constant of −0.1. When an ophthalmoscopy lens device having these parameter values is placed on an emmetropic eye, an aerial image of the patient's retina will be produced approximately 9.65 mm anterior of the image forming lens.

FIG. 3 shows another alternative lens layout design that could be used in place of that shown in FIG. 1. In FIG. 3, posterior lens portion 24" has a concave anterior surface 30" and anterior lens portion 26" has a matching convex posterior surface 32". An exemplary configuration of the embodiment in FIG. 3 has the same parameter values as in the exemplary configuration described above in connection with FIG. 1, except that the concave anterior surface 30" of posterior lens portion 24" and the convex posterior surface 32" of anterior lens portion 26" each have a radius of 45 mm, and the conic constant of the anterior surface 34" of anterior lens portion 26 is −0.9. When an ophthalmoscopy lens device having these parameter values is placed on an emmetropic eye, an aerial image of the patient's retina will be produced approximately 9.0 mm anterior of the image forming lens.

The lens layout design of FIG. 3 provides a wide field of view, although not quite as wide with respect to the design of FIGS. 1 and 2. That is, when the mating surfaces 30", 32" are curved, as shown in FIG. 3, some of the most peripheral rays exiting the eye do not intercept the interfaced surfaces, as shown for example by ray 48 in FIG. 3.

FIG. 4 illustrates an indirect ophthalmoscopy contact lens device having a multi-element lens design incorporating a middle meniscus element 54. This alternative design provides an even wider field of view compared to the previously described embodiments, although at the expense of greater complexity and potentially increased surface reflections. The wider field is afforded in this embodiment by provision of middle meniscus element 50 which further bends the light rays, in particular, the peripheral light rays, so that they can be collected and focussed by image forming lens 14". In an exemplary configuration of the lens design in FIG. 4, the plastic posterior lens portion 24''' is made of the same PMMA material as mentioned above and anterior lens portion 26''', as well as meniscus lens 50 and image forming lens 14" are made of LAH58 glass. Posterior lens portion 24''' has a concave posterior surface 28' with a 7.7 mm radius, a convex anterior surface 30''' having a radius of 20 mm and a center thickness of 1.0 mm. Anterior lens portion 26''' has a posterior concave surface 32''' with the same radius as mating surface 30''' an anterior surface 34''' with an apical radius of 8.5 mm and a conic constant of −0.1, and a center thickness of 4 mm and diameter of 16.6 m. Meniscus lens 50 is spaced 0.5 mm in an anterior direction from lens portion 26'''. Meniscus lens 50 has a center thickness of 3.0 mm, a posterior concave surface 52 having a radius of 27.5 mm, and an anterior convex surface 54 having a radius of 16 mm. Meniscus lens 50 has a diameter of 24 mm. Image forming lens 14" is spaced by 0.5 mm in an anterior direction from meniscus lens 50. Image forming lens 14" has a posterior convex surface 36" with a radius of 200 mm, a convex anterior surface 38" with an apical radius of 24 mm and a conic constant of −2.47, a center thickness of 5.5 mm and a diameter of 28 mm. It is understood that the three lenses illustrated in FIG. 4 and additionally the lenses illustrated in FIGS. 2 and 3 would be suitably fixed in a housing similar to the fixation of the lenses in FIG. 1. When an ophthalmoscopy device having the lens design shown in FIG. 4 and the parameter values described above is placed on an emmetropic eye, the aerial image will be slightly concave viewed from the anterior direction and will be spaced from the anterior surface of image forming lens 14 by approximately 8.75 mm.

The specific configurations discussed above in connection with the embodiments of FIGS. 1 to 4 are by way of example only. The essence of the invention as depicted in these figures is an indirect ophthalmoscopy contact lens device wherein the contact lens element is a compound lens element in which a high index of refraction anterior lens portion is cemented to a lower index of refraction posterior lens portion to produce substantial light bending at the interface of the two lens portions so that peripheral light rays emanating from the retina are bent inwardly to be captured by the subsequent or final image forming lens to provide a wide field, high resolution aerial image of the fundus.

The indirect ophthalmoscopy contact lens device of the invention can be used with a slit lamp biomicroscope for both diagnosis and laser treatment to the far peripheral quadrants of the retina and can also be used with an operating microscope in conjunction with vitreo retinal surgery. Such a lens for vitreo retinal surgery may be hand-held by a physician's assistant with the use of a detachable handle or by placing the lens in a suture down vitrectomy ring as will be understood by those skilled in the art.

A lens made according to the embodiment of FIG. 1 will produce a field of view of approximately 140° with an image magnification of about 0.54. The ophthalmoscopy device according to FIGS. 2 and 4 will have a greater field of view compared to FIG. 1 and the embodiment in FIG. 3 will have a slightly narrower field of view compared to FIG. 1.

FIG. 5 shows a contact ophthalmoscopy lens particularly well suited for many types of vitreoretinal surgery including membranectomy, repair of retinal detachment and vitrectomy. By providing a very wide field of view in an appropriately scaled down size, the high power of the lens combined with an uninterrupted global fundus view make it ideal for use with an image reinverting system combined with the operating microscope. In FIG. 5, as well as FIG. 6 discussed below, only the chief rays are shown in order to more clearly define the back focus of the indirect ophthalmoscopy contact lens system.

In an exemplary configuration of the lens design in FIG. 5, compound contact lens element 112 includes a posterior lens portion 124 made of the same PMMA material as mentioned above and an anterior lens portion 126 made of LAH58 glass. Posterior lens portion 124 has a concave posterior surface 128 with a 7.7 mm radius and conic constant of −0.18, a flat anterior surface 130 and a center thickness of 0.25 mm. Anterior lens portion 126 is made of LAH58 glass and has a correspondingly flat posterior surface 132, an anterior surface 134 with an apical radius of 7.7 mm and conic constant of −0.2, a center thickness of 4 mm and diameter of 13.4 mm. The outside diameter of the posterior lens portion 124 is 11.45 mm, which is compatible for placement in a typical suture down vitrectomy ring.

Image forming lens 114 is spaced by 0.5 mm in an anterior direction from anterior surface 134 of anterior portion 126 and is also made of LAH58 glass. Image forming lens 114 has a posterior convex surface 136 with an apical radius of 45 mm and conic constant of −8.0, a convex anterior surface 138 with an apical radius of 24 mm and a conic constant of −2.5, a center thickness of 4.0 mm and a diameter of 18 mm. When an indirect ophthalmoscopy lens constructed according to the above parameters is placed on an emmetropic eye, a slightly concave aerial image will be produced approximately 6 mm anterior of image forming lens 114.

In some instances, particularly in focal laser treatment and in vitreoretinal surgery close to the macular area, it may be desirable to provide an increased depth of field and improved image resolution to enhance the view of fine retinal detail in the central retinal area, at the expense of a slightly decreased field of view. The principles of the invention incorporating a compound contact lens element comprised of an anterior lens portion cemented to a posterior lens portion with different optical properties provides an advantageous configuration for producing a high quality aerial image. In such a configuration, the posterior lens portion will preferably be of a highly dispersive optical material having an Abbe value in a range from about 20 to 50 and the anterior lens portion will have a higher Abbe value in a range from about 40 to 90. In this way, the negative chromatic aberration resulting from the posterior lens portion will help to counteract the positive chromatic aberration or positive dispersion of the successive positive power lens elements.

FIG. 6 shows a lens layout for an indirect ophthalmoscopy contact lens device for achieving increased magnification and resolution, as well as providing reduced chromatic aberration, as discussed above. In this embodiment, the posterior lens portion 224 of contact lens element 212 has a center thickness that is relatively larger than the center thickness of the previously described lens designs, so that anterior lens portion 226 is not as close to the corneal surface as in the previous designs. In an exemplary configuration of the embodiment in FIG. 6, posterior lens portion 224 has a concave posterior surface 228 with an apical radius of 7.7 mm and conic constant of −0.18 to substantially correspond to the shape of an average cornea. Again, the outside diameter of posterior lens portion 224 is 11.45 mm, suitable for placement in a typical suture down vitrectomy ring. Anterior surface 230 of posterior lens portion 224 has a concave shape with a radius of curvature of 25 mm and mating posterior surface 232 of anterior lens portion 226 has a corresponding convex radius of curvature. Posterior lens portion 224 in this embodiment has a center thickness of 2 mm and anterior lens portion 226 has a center thickness of 4 mm. Anterior lens portion 226 has an anterior surface 238 with an apical radius of 8 mm and a conic constant of −0.355. Posterior lens portion 224 is made of F5 glass manufactured by Schott Glass and has an index of refraction of 1.603 with an Abbe value of 38.03, and anterior lens portion 226 in this case is made of SK16 glass, also manufactured by Schott Glass and has an index of refraction of 1.62 with an Abbe value of 60.32. The diameter of anterior lens portion 226 is 12.4 mm. As an alternative to the F5 glass, polystyrene or polycarbonate plastic may be used in the design of the posterior contact lens portion. Image forming lens 214 is made from BK7 glass having an index of refraction of 1.517 and an Abbe value of 64.17, and is spaced in an anterior direction from contact lens element 212 by 4 mm. Image forming lens 214 has a center thickness of 5 mm, a posterior surface 236 with an apical radius of 23 mm and conic constant of −1.7, an anterior surface 238 with an apical radius of 23 mm and a conic constant of −0.9131 and diameter of 18 mm. The total physical length of the ophthalmoscopic lens system is 16.8 mm. When an indirect ophthalmoscopy device having a lens design according to FIG. 6 is placed on an emmetropic eye, an essentially flat, but slightly concave aerial image is produced spaced in the anterior direction from image forming lens 214 by approximately 14.3 mm. A lens design according to FIG. 6 having the foregoing parameters will produce an image magnification of approximately 0.82 and has the advantage of reducing chromatic aberration as previously discussed.

A further advantage of this lens design relates to its reduced overall length compared to other designs providing similar magnification. By positioning the back focus of the lens beyond the eye pupil of the patient by approximately 3 mm, as represented by focal point 239, the distance between lens 226 and lens 214 will be correspondingly reduced, minimizing the overall height of the lens system when on the eye, for added working room and safety during vitreoretinal surgery. Although some clipping or vignetting of ray bundles from the peripheral retina may occur by the pupil iris, there will be little or no detrimental effect on the quality of the more central retinal view as visualized through the operating microscope.

Figure 7:
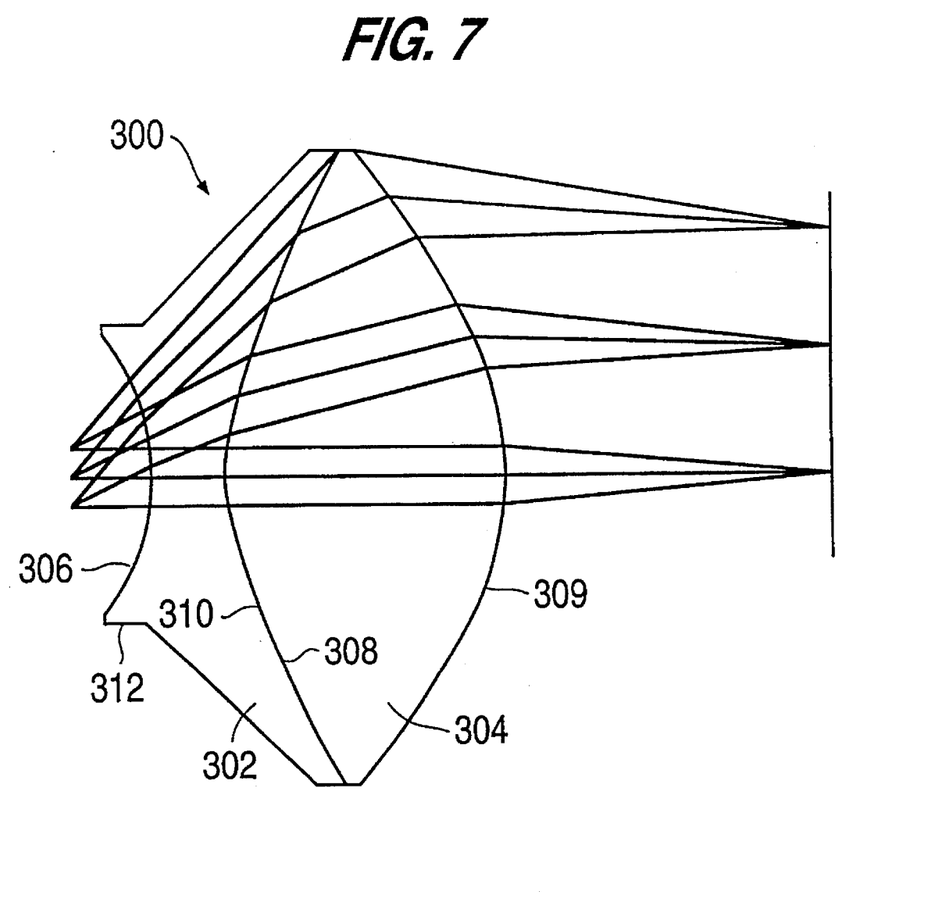
FIG. 7 is a diagram showing a lens layout and ray tracing according to another embodiment of the invention in which the image forming lens is integrated into the compound contact lens element.

FIG. 7 shows an indirect ophthalmoscopy lens utilizing the principles of the invention employing a compound contact lens element, wherein the anterior lens portion of the compound contact lens element itself comprises the image forming lens. The elimination of the air space between the compound lens element and the image forming lens that is present in the prior embodiments concomitantly and advantageously eliminates the need for an air-tight, waterproof housing. Eliminating the air space by joining together the image forming lens element and the contact lens element to produce a single lens device also avoids the need for coating both interface surfaces, as previously discussed, and results in a device in which reflections are minimized with essentially only the outer most (anterior) surface as the source for any unwanted reflections.

Referring to FIG. 7, there is shown a compound contact lens element 300 including a posterior lens portion 302 and a convex anterior lens portion 304 cemented to the posterior lens portion. In an exemplary configuration, posterior lens portion 302 is made of plastic, preferably PMMA having an index of refraction of 1.491, and has a concave posterior lens surface with a radius of curvature of 7.7 mm, a concave anterior lens surface 308 having a curvature that closely matches the convex curvature of posterior lens surface 310 of anterior lens portion 304 and a center thickness of 3.0 mm. Desirably, posterior lens portion 302 has a short cylindrical region 312 with a diameter of 11.45 mm which renders the lens suitable for being fitted into a suture down vitrectomy ring for vitreoretinal surgery.

Biconvex anterior lens portion 304 is made of LAH58 glass having an index of refraction of 1.883. Posterior lens surface 308 has an apical radius of 11.0 mm with a conic constant of −9.3091, and is further defined, with reference to the foregoing formula, by second, fourth and sixth higher order terms, wherein the corresponding coefficients are $a_2 = -0.01984681$, $a_4 = 4.606164 \times 10^{-5}$, and $a_6 = -5.627951 \times 10^{-8}$. The mating acrylic concave anterior lens surface 308 of posterior lens portion 302 need not be produced according to the polynomial curve defined by the above coefficients. Instead, concave surface 308 may be produced as a best fit, or approximate conic, because the optical cement used to join the mating surfaces will match the index of refraction of the acrylic, in effect extending the acrylic surface to conform and match precisely, with intimate contact, the complex aspheric surface of the posterior side of glass anterior lens portion 304.

Anterior lens portion 304 further includes a convex anterior lens surface 309 having an apical radius of 7.358 mm with a conic constant of −1.0793 and is also defined by second, fourth and sixth higher order terms having corresponding coefficients of $a_2=0.01271833$, $a_4=4.371391\times10^{-5}$ and $a_6=-1.096848\times10^{-7}$. Anterior lens portion 304 has a center lens thickness of 11.0 mm and a diameter of 22.0 mm.

The compound contact lens indirect ophthalmoscopy device of FIG. 7 can be used with or without a housing. If a housing is employed, the housing (not shown) may extend beyond the glass portion, making it suitable as a handheld lens for use with a slit lamp. Additionally, the diameter of the posterior side of the posterior portion may be suitably increased, and may include an eyelid flange, as is common practice. A variety of powers can be produced, including much longer focal length systems providing a magnification of 1.0 and greater, as would be obvious to the ordinarily skilled lens designer.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. In an indirect ophthalmoscopy contact lens device including a contact lens having a first posterior lens surface with a concave shape substantially corresponding to the shape of an average cornea and an image forming lens for collecting and focussing light exiting the patient's eye through the contact lens when in place on the patient's eye for forming an aerial image of the fundus of the patient's eye, the improvement wherein:
the contact lens comprises a compound contact lens element including:
a posterior lens portion including said first posterior lens surface and a first anterior lens surface, said posterior lens portion being made of a material having a first index of refraction and a first Abbe value;
an anterior lens portion having a second posterior lens surface with a shape substantially matching a shape of the first anterior lens surface and a second anterior lens surface having a convex shape, said anterior lens portion being made of a material having a second index of refraction and a second Abbe value, at least one of the second index of refraction and the second Abbe value being different from the first index of refraction and the first Abbe value, respectively; and
an optical cement having a third index of refraction corresponding to one of the first and second indexes of refraction for fixing in intimate contact the second posterior lens surface to the first anterior lens surface.

2. The device according to claim 1 wherein the index of refraction of the anterior lens portion is greater than the index of refraction of the posterior lens portion.

3. The device according to claim 2, wherein the posterior lens portion is comprised of plastic and the anterior lens portion is comprised of glass.

4. The device according to claim 2, wherein the second index of refraction is in a range from about 1.52 to about 2.1.

5. The device according to claim 2, wherein the first index of refraction is in a range from about 1.3 to about 1.52.

6. The device according to claim 2, wherein a difference between the first and second indexes of refraction is equal to or greater than 0.27.

7. The device according to claim 2, wherein the posterior lens portion of the compound contact lens element has a thickness in its central region in a range from about 0.125 mm to about 2.0 mm.

8. The device according to claim 2, wherein the first anterior lens surface and the second posterior lens surface are substantially planar.

9. The device according to claim 2, wherein the first anterior lens surface has a convex shape and the second posterior lens surface has a matching concave shape.

10. The device according to claim 2, wherein the first anterior lens surface has a concave shape and the second posterior lens surface has a matching convex shape.

11. The device according to claim 2, further comprising a housing, wherein said compound contact lens element is mounted in said housing and said image forming lens comprises a separate lens mounted in said housing space apart in an anterior direction from said compound contact lens element.

12. The device according to claim 11, wherein at least one surface of the image forming lens is aspheric.

13. The device according to claim 12, wherein the at least one aspheric surface is defined by the following formula $$z = \frac{cr^2}{1 + \sqrt{1-(1+k)c^2r^2}} + a_1r + a_2r^2 + a_3r^3 \ldots a_nr^n$$

where z equals the surface sag along the lens axis, c equals the curvature (i.e., reciprocal of the radius), r is the radial coordinate in lens units, k equals the conic constant, $n=1,2,\ldots,a_nr^n$ are higher order conic deformation terms, and $a_n$ represents a coefficient values of respective conic deformation terms.

14. The device according to claim 13, wherein at least one higher order deformation term has a non-zero value.

15. The device according to claim 11, wherein the second index of refraction is in a range from about 1.52 to about 2.1.

16. The device according to claim 11, wherein the first index of refraction is in a range from about 1.3 to about 1.52.

17. The device according to claim 11, wherein a difference between the first and second indexes of refraction is equal to or greater than 0.27.

18. The device according to claim 11, wherein the posterior lens portion of the compound contact lens element has a thickness in its central region in a range from about 0.125 mm to about 2.0 mm.

19. The device according to claim 11, wherein the first anterior lens surface and the second posterior lens surface are substantially planar.

20. The device according to claim 11, wherein the first anterior lens surface has a convex shape and the second posterior lens surface has a matching concave shape.

21. The device according to claim 11, wherein the first anterior lens surface has a concave shape and the second posterior lens surface has a matching convex shape.

22. The device according to claim 11, and further including a plus powered middle lens element mounted in the housing between the compound contact lens element and the image forming lens for bending light exiting from the second anterior lens surface toward a center axis of the device.

23. The device according to claim 22, wherein the middle element has a meniscus shape.

24. The device according to claim 12, wherein the second anterior lens surface of the anterior lens portion is aspheric.

25. The device according to claim 24, wherein the aspheric second anterior lens surface is defined by the following formula $$z = \frac{cr^2}{1 + \sqrt{1 - (1+k)c^2r^2}} + a_1r + a_2r^2 + a_3r^3 \ldots a_nr^n$$

where z equals the surface sag along the lens axis, c equals the curvature (i.e., reciprocal of the radius), r is the radial coordinate in lens units, k equals the conic constant, n=1,2,..., $a_nr^n$ are higher order conic deformation terms, and $a_n$ represents coefficient values of respective conic deformation terms.

26. The device according to claim 2, wherein said anterior lens portion is biconvex and itself comprises the image forming lens.

27. The device according to claim 26, wherein the second anterior lens surface is aspheric.

28. A device according to claim 27, wherein the aspheric second anterior lens surface is defined by the following formula $$z = \frac{cr^2}{1 + \sqrt{1 - (1+k)c^2r^2}} + a_1r + a_2r^2 + a_3r^3 \ldots a_nr^n$$

where z equals the surface sag along the lens axis, c equals the curvature (i.e., reciprocal of the radius), r is the radial coordinate in lens units, k equals the conic constant, n=1,2,..., $a_nr^n$ are higher order conic deformation terms, and $a_n$ represents coefficient values of respective conic deformation terms.

29. The device according to claim 28, wherein at least one higher order deformation term has a non-zero value.

30. The device according to claim 28, wherein the second posterior lens surface is aspheric.

31. The device according to claim 11, wherein the posterior lens portion is comprised of plastic and the anterior lens portion is comprised of glass.

32. The device according to claim 1, wherein the posterior lens portion has negative optical power and is highly color dispersive and the anterior lens portion has positive optical power and has reduced color dispersion.

33. The device according to claim 32, wherein the first Abbe value is lower than the second value and the first Abbe value of the posterior lens portion is in a range from about 20 to 50 and the second Abbe value of the anterior lens portion is in a range from about 40 to 90, thereby reducing or minimizing chromatic aberration of the indirect ophthalmoscopy contact lens device.

34. The device according to claim 1, wherein said device has a posterior focus located behind the patient's pupil and within the crystalline lens or vitreous humor of the patient's eye.

35. A method of performing ophthalmoscopic procedures and laser treatment, comprising utilizing the device according to claim 1 in conjunction with a slit lamp biomicroscope.

36. A method of performing vitreoretinal surgery of the eye, comprising utilizing the device according to claim 1 in conjunction with an operating microscope.

37. The device according to claim 1, wherein said anterior lens portion comprises the image forming lens.

* * * * *

(12) REEXAMINATION CERTIFICATE (4310th)
United States Patent
Volk (10) Number: US 5,523,810 C1
(45) Certificate Issued: Apr. 17, 2001

(54) INDIRECT OPHTHALMOSCOPY CONTACT LENS DEVICE WITH COMPOUND CONTACT LENS ELEMENT

(75) Inventor: Donald A. Volk, Mentor, OH (US)

(73) Assignee: Volk Optical, Inc., Mentor, OH (US)

Reexamination Request:
No. 90/005,763, Jun. 29, 2000

Reexamination Certificate for:
Patent No.: 5,523,810
Issued: Jun. 4, 1996
Appl. No.: 08/465,641
Filed: Jun. 5, 1995

(51) Int. Cl.$^7$ ..................................................... A61B 3/00
(52) U.S. Cl. ........................................... 351/219; 351/205
(58) Field of Search .................................... 351/205, 212, 351/219, 160 R, 161, 160 H; 606/4, 5, 6

(56) References Cited

U.S. PATENT DOCUMENTS 4,302,081 * 11/1981 Tsuetaki .............................. 361/161

FOREIGN PATENT DOCUMENTS

1 188 326   3/1965 (DE) .

\* cited by examiner

Primary Examiner—G. Manuel (57) ABSTRACT

An indirect ophthalmoscopy contact lens device includes a contact lens having a first posterior lens surface with a concave shape substantially corresponding to the shape of an average cornea and an image forming lens for collecting and focussing light exiting the patient's eye and entering the contact lens when in place on the patient's eye for forming an aerial image of the fundus of the patient's eye. The contact lens comprises a compound contact lens element including a posterior lens portion cemented to an anterior lens portion. The posterior lens portion includes the first posterior lens surface and a first anterior lens surface, and is made of a material having a first index of refraction and a first Abbe value. The anterior lens portion has a second posterior lens surface with a shape substantially matching a shape of the first anterior lens surface and a second anterior lens surface having a convex shape. The anterior lens portion is made of a material having a second index of refraction and a second Abbe value. At least one of the second index of refraction and the second Abbe value is different from the first index of refraction and the first Abbe value, respectively. The optical cement preferably has an index of refraction corresponding to the first or second index of refraction.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–37 is confirmed.

\* \* \* \* \*